United States Patent
Terenzio et al.

(10) Patent No.: US 10,301,229 B2
(45) Date of Patent: May 28, 2019

(54) PROCESS FOR THE PREPARATION OF HUMIC EXTRACTS FROM FOSSIL SOURCES

(71) Applicant: Best Green Technologies Inc., Miami Beach, FL (US)

(72) Inventors: Domenico Terenzio, Fondi (IT); Aldo Perotti, Terracina (IT)

(73) Assignee: Best Green Technologies Inc., Miami Beach, FL (US)

( * ) Notice: Subject to any disclaimer, the term of this patent is extended or adjusted under 35 U.S.C. 154(b) by 75 days.

(21) Appl. No.: 15/322,440

(22) PCT Filed: Jun. 27, 2014

(86) PCT No.: PCT/US2014/044703
§ 371 (c)(1),
(2) Date: Dec. 27, 2016

(87) PCT Pub. No.: WO2015/199733
PCT Pub. Date: Dec. 30, 2015

(65) Prior Publication Data
US 2017/0152195 A1    Jun. 1, 2017

(51) Int. Cl.
*C05F 11/02* (2006.01)
*C05F 11/10* (2006.01)
*A01N 65/20* (2009.01)
*A01N 65/26* (2009.01)
*C05B 17/00* (2006.01)
*C05C 11/00* (2006.01)
*C05G 3/00* (2006.01)
*C05G 3/02* (2006.01)

(52) U.S. Cl.
CPC .............. *C05F 11/02* (2013.01); *A01N 65/20* (2013.01); *A01N 65/26* (2013.01); *C05B 17/00* (2013.01); *C05C 11/00* (2013.01); *C05F 11/10* (2013.01); *C05G 3/00* (2013.01); *C05G 3/02* (2013.01)

(58) Field of Classification Search
None
See application file for complete search history.

(56) References Cited

U.S. PATENT DOCUMENTS

| | | | |
|---|---|---|---|
| 6,287,496 B1 * | 9/2001 | Lownds | C05F 11/02 264/118 |
| 2002/0121046 A1 | 9/2002 | Yamashita | |
| 2006/0168881 A1 | 8/2006 | Straumietis | |
| 2006/0169014 A1 * | 8/2006 | Brenuy | C05C 5/02 71/24 |
| 2007/0051148 A1 | 3/2007 | Terenzio | |
| 2008/0216534 A1 | 9/2008 | Karr | |
| 2009/0078014 A1 | 3/2009 | Yamashita | |
| 2009/0082205 A1 * | 3/2009 | Stock | A01G 25/092 504/117 |
| 2014/0349847 A1 * | 11/2014 | Schrader | C05F 11/02 504/100 |

FOREIGN PATENT DOCUMENTS

| | | |
|---|---|---|
| EP | 0298136 A1 | 1/1989 |
| WO | 2013109153 A1 | 7/2013 |

OTHER PUBLICATIONS

International Search Report in PCT/US/1444703 dated Jan. 16, 2015.
International Report on Patentability in PCT/US144703 dated Dec. 27, 2016.
Written Opinion of the International Searching Authority in PCT/US144703 dated Jan. 16, 2015.

* cited by examiner

Primary Examiner — Wayne A Langel
(74) Attorney, Agent, or Firm — Henry J. Cittone; Cittone Demers & Arneri LLP

(57) ABSTRACT

The present invention relates to a process for the preparation of fertilizing compositions and to the compositions obtained.

12 Claims, No Drawings

PROCESS FOR THE PREPARATION OF HUMIC EXTRACTS FROM FOSSIL SOURCES

CROSS-REFERENCE TO RELATED APPLICATIONS

This application is the U.S. National Stage of PCT International Patent Application No. PCT/US2014/044703, filed Jun. 27, 2014, the disclosures of which are incorporated herein by reference in their entirety.

BACKGROUND OF THE INVENTION

There are known in the art numerous fertilizing formulations based on humates and/or humic extracts obtained from fossil sources. However, said formulations have problems both from a qualitative and a quantitative point of view, in that they lead to unsatisfactory agronomic results.

Humic acids have important functions in both soil and plants. In soil they bind to macro and micro elements, in particular to phosphorus and iron, enhancing their bioavailability to plants and at the same time avoiding insolubilization caused by high pH and high percentages of active limestone. In addition, they enhance biodegradation of toxins produced by plants, of active compounds and of many pollutants of organic origin.

They also improve the chemical, physical and biological properties of the soil, increasing the carbon of biological origin, which acts as an important catalyst in the process of assimilation of nutrients to crops.

More generally, humic acids are known to promote seed germination, development and fortification of the root system, as well as improving the overall biochemical activities of the plant and soil. U.S. Pat. No. 4,698,090 describes a process for the preparation of a liquid composition used to improve the growth of plants, in which a leonardite based mineral is reacted with an organic chelating agent in aqueous medium at a temperature between 77-107° C. Among the chelating agents used are, for example, gluconic acid, glucaric acid, glutaric and glutamic acid or glutamine and synthetic chelating agents such as EDTA.

U.S. Pat. No. 4,786,307 describes a process for the preparation of liquid fertilizers, in which the product obtained after the extraction of the leonardite base material in water with a chelating agent consisting of a salt of a hydroxy acid at a pH>2.5 is combined with a metal salt of a micro-nutrient metal in the presence of a hydroxy acid with the subsequent addition of anhydrous ammonia in the reaction mixture in order to bring the pH to value between 7.5 and 9. The synthetic chelating agents include: ethylenediamine acid-N-bis(2-hydroxyphenylacetic) (EDDHA), ethylenediaminetetraacetic acid (EDTA), and diethylenetriaminepentaacetic acid (DTPA) and are characterized by a very high environmental impact. In fact, they are quickly leached away into the ground water and thus could pollute the waters and the soil.

PCT International Application WO 2004/110962 describes a process for the preparation of fertilizers in solid and liquid form based on fossil materials, having a high content of humic acids, in particular leonardite, characterized by the use of water and gluconic acid and the subsequent extraction of the humic acids in the presence of an alkaline agent such as potassium hydroxide or ammonium until obtaining a pH>9.

PCT International Application WO 2010/013275 describes a process for the formulation of compositions of natural fertilizers and surfactants for washing, reclamation and cultivation of contaminated soils and compositions in liquid and solid form comprising the use of alginic acid and, as a means of extracting potassium hydroxide or ammonium hydrate or their association, to obtain a product with an extremely high pH.

In light of the above, environmentally friendly technological formulations, such as fertilizers and resistance inducers, which overcome the many disadvantages of the formulations known in the art are needed.

SUMMARY OF THE INVENTION

Aspects of the present invention include new fertilizer formulations based on complex of humic and/or fulvic acids. The formulations obtained have very high functionality, allowing improvement of the quality and quantity of treated cultures compared to known fertilizer compositions.

Aspects of the present invention make it possible to obtain compositions characterized by a very high effectiveness, while being environmentally sustainable thanks to the use of raw materials characterized by the absence of toxicity towards humans, animals and the ecosystem.

OBJECT OF THE INVENTION

It is an object of the present invention to provide a process for the preparation of fertilizing compositions obtained from fossil raw materials. It is a further object of the present invention to provide a process for preparing a base fertilizing composition and improved fertilizing compositions.

It is another object of the present invention to provide base and improved fertilizing compositions obtained according to the disclosed process.

It is yet another object of the present invention to provide fertilizing compositions comprising a base fertilizing composition and/or an improved fertilizing composition and one or more other active principles used in agriculture.

It is yet another object of the present invention to provide slow-release fertilizing compositions.

DETAILED DESCRIPTION OF THE INVENTION

According to a first embodiment of the invention, a process for the preparation of a base fertilizing composition is disclosed.

In a preferred embodiment, said process comprises the steps of:

a) preparing a muddy mixture of a fossil base material and water;
b) adding to said muddy mixture citric acid;
c) adding an alkaline solution of potassium bicarbonate and folic acid.

In a particular embodiment, in step a) above, the fossil base material is selected in the group comprising leonardite, lignite, peat humus, xilite, coal peat and brown coal, or mixtures of one or more of said base materials.

In a preferred embodiment, the fossil base material is leonardite.

In certain embodiments, the fossil base material is characterized by a content of at least 45% and preferably of at least 60% of organic content.

In a preferred embodiment, the organic content of the fossil base material is of at least 80% and even more preferably of at least 90%.

The term "organic content" is used herewith to refer to the whole content of carbonium of biological origin (it is internationally recognized that in order to estimate the total content of organic substance from the organic carbonium of vegetal origin, a factor of 1.724 of total organic carbonium, sometimes a factor of 2, is used).

In certain embodiments of the invention, the fossil base material is in the form of a powder.

In particular, the size of the powder particles is between about 100 and 200 mesh and preferably of between 100 and 150 mesh.

The size of the particles is selected depending upon the type of formulation desired: solid or liquid.

In an embodiment, the base material and water are mixed together in step a) in a ratio comprised between about 1:0.1 to about 1:10.

In a preferred embodiment, the ratio is comprised between 1:0.2 and 1:8 and in an even more preferred embodiment, the ratio is comprised between 1:0.3 and about 1:6.

In particular, the relative quantity of fossil base material and water determines the preparation of a solid or a liquid fertilizing formulation.

For example, when the fossil base material:water ratio used is of about 1:0.3 then a solid formulation is preferably obtained.

When the fossil base material:water ratio is used of about 1:6 then a liquid formulation is preferably obtained.

According to a preferred embodiment, the water used for the preparation of the muddy mixture is demineralized water.

"Demineralized water" refers to water deprived of mineral (salt) components.

According to a preferred embodiment, in step b) the citric acid is added in an amount comprising between about 1-7% (w/total weight of the final composition) and preferably of between 3-5%.

During the addition of citric acid, the mixture is preferably kept stirring until complete homogenization.

In an embodiment of the invention, citric acid is used in the form of monohydrate citric acid.

Monohydrate citric acid is preferably pure.

According to an embodiment of the invention, step c) comprises the addition of folic acid in an amount comprising between about 0.5-6% (w/total weight of the composition).

Preferably, the folic acid is added in an amount comprised between about 1-4% (w/total weight of the composition).

In the present invention, the amount of the components is referred to as weight versus the total weight of the composition (made to 100%).

In certain embodiments of the invention, pure folic acid is used (pharmaceutical technical grade).

In an embodiment, in the above step c) the potassium bicarbonate is added is a quantity of between 5-20% (w/total weight of the composition).

According to a preferred embodiment, the potassium bicarbonate added is a quantity of between 8-15% (w/total weight of the composition).

In an embodiment of the invention, potassium bicarbonate is used as a pure salt.

In an alternative embodiment, potassium hydroxide is used instead of potassium bicarbonate.

In a preferred embodiment of the invention, the final pH of the fertilizing compositions is between about 6.0-7.5.

In an embodiment of the invention, the process allows for obtaining a solid fertilizer composition.

In other embodiments, the process allows for obtaining a liquid fertilizer composition.

In one embodiment, a process for the preparation of solid fertilizer compositions is disclosed, where the process of the invention comprises after step c):

a step d1) of subjecting the muddy composition obtained from step c) to granulation or pelletisation; and a step e1) of drying.

In certain embodiments, the granulation is performed in a disc or blade granulator.

Drying can be performed for example in a rotating dryer or in a fluid bed dryer.

In a preferred embodiment of the invention, the improved fertilizing compositions are formulated as solid formulations.

For example, they can be in the form of powder, microgranules, granules, pellets and the like. Powder formulations comprise particles having a medium size of 0.01 mm e 0.1 mm.

Microgranule formulations comprise particles having a medium size of 0.5 mm e 1.2 mm.

Granule formulations comprise granules having a medium size of about 2-2.5 mm and preferably of 2.5 mm.

The use of granule formulations is especially suitable for ornamental plants, turfs and lawns, fruits.

In certain embodiment of the invention the preparation of liquid fertilizing compositions is disclosed. In particular, for said purpose, the process of the invention preferably comprises in step a) the use of a base fossil material having a grain size of about 100-150 mesh. In addition to that, after step c) a step d2) for separating the solid particles and other insoluble materials is performed. In an embodiment of the invention, said separation is performed by methods and techniques known by a person of skill in the art, for example, by filtration or by decanting.

In an embodiment of the invention, the formulation is left decanting for a period of 3-7 days and preferably for 5 days.

According to an embodiment, the composition obtained according to the process of the invention is a base fertilizing composition.

In other embodiments, improved fertilizing compositions can be obtained.

In particular, said improved compositions are obtained by adding in the process step a) one or more substances selected from the group comprising: macroelements, microelements, mesoelements, nutritional catalyzers, proteic hydrolyzed of animal or vegetal origin and other substances endowed with specific activity like repellents against insects, nematodes, fungicidal activity, fungistatic activity, bactericidal activity and bacteriostatic activity, plant growth regulators and complex fertilizers. Among macroelements there are included for example nitrogen, phosphorus and potassium.

Among microelements there are included for example iron, zinc, manganese, copper, boron, molybdenum. Among mesoelements there are included: calcium and magnesium.

In particular embodiments of the invention the improved fertilizing compositions include for example: nitrogen humofolate, phosphorus humofolate, nitrogen and phosphorus humofolate, nitrogen phosphorus and potassium humofolate, potassium humofolate, iron humofolate, boron humofolate, molybdenum humofolate, zinc humofolate, manganese humofolate, copper humofolate, humofolate with mixtures of microelements, amino acids humofolate, vegetal extracts humofolate.

Further improved compositions are obtained by addition of suitable sources of nitrogen, phosphorus, potassium, iron, boron, molybdenum, zinc, manganese, copper or other microelements.

For example, urea compounds, sulphate compounds, phosphate compounds, phosphite compounds, carbonate compounds, oxide compounds can be used.

Urea compounds include urea.

Preferably, the urea has a low content of biuret, like for example less than 1%, preferably less than 0.5% and even more preferably less than 0.4%.

In other embodiments, monoammonium phosphate, zinc sulphate, manganese sulphate, boron etanolamine, phosphorus pentaoxide, potassium oxide are used.

Among nutritional catalyzers there are included: algae and vegetal extracts, which are obtained by chemical or enzymatic hydrolysis and have high phytostimulating and/or protective activity (both apogee or hypogeal) on plants.

Among proteic hydrolyzed of animal origin there are included: fleshings, blood derivatives.

Among plant regulators there are included: cytokinines, auxins, gibberellerines, etc.

In an embodiment of the invention, vegetable cakes obtained from the extraction of oils, like for example, neem oil (Azadirachta indica), karanja oil (Pongamia glabra), castor oil (Ricinus communis) and Jatropha oil (Jatropha curcas), can be added to the base fertilizing formulation of the invention.

In certain embodiments of the invention, the improving substances are added in an amount of <70%, preferably less the 60% (w/total weight of the composition).

In other embodiments of the invention, the base or the improved fertilizer compositions disclosed can be used for the preparation of complex compositions comprising, for example, mineral fertilizing compositions, organic fertilizing compositions or other active principles used in agriculture or plant cultivation, alone or in mixture.

According to an additional embodiment of the invention, the granular and microgranular formulations are added with substances capable of improving the water retention and increasing the bioavailability of the nutrients.

In particular, said formulations comprise absorbing substances of natural or synthetic origin.

Natural substances include for example starches and derivatives thereof.

Synthetic substances comprise potassium polyacrylates.

In preferred embodiments, said substances are added to the formulation is an amount comprised between about 5% and 20% (weight percentage on the total weight of the composition).

According to certain embodiments of the invention, there are disclosed slow-release fertilizing compositions produced as per the method of the invention.

In fact, the humic acids in the formulations of embodiments of the invention are in a complexed form, which enables a slow-release into the soil.

In an embodiment of the invention, the use of the above compositions as fertilizers is disclosed. In particular, said formulations can be used on crops, food crops, industrial crops, bioenergetics crops.

Food crops include for example salad, lattuce, rocket, celery, valerian, tomato, pepper, eggplant, potato, little bean, bean, cucumber, radish, squash, carrot, strawberry, watermelon, melon, wheat, barley, quinoa, corn, soybeans, rape, sunflower, sugar beet, rice, peanuts, tobacco, plum, kiwi, apple, pear, banana, cherry, peach, apricot, papaya, mango, pineapple, pomegranate, berries, (blackberry, raspberry, blueberry), grapevine, citrus, the, coffee, cocoa.

Industrial crops include for example cotton, sugar beet, sugar cane, rapeseed, sunflower, corn, soya, rape, peanuts, wheat, barley.

Bioenergetic crops include for example soybean, rapeseed, sunflower, Jatropha curcas.

In other embodiments, the formulations of the invention may be used on turfs, ornamental plants, nursery, growing plants in hydroponic cultivations. More in particular, said formulations can be used in any soil and climate conditions.

In an additional embodiment, the use of the compositions of the invention as resistance inducers is disclosed.

In particular, formulations of the invention allow a higher resistance of the crops against bacteria and fungi.

In fact, it has been observed that plants treated with at least some of the compounds of the invention increase the production of phytoalexines and other proteins providing a specific resistance.

In particular, it has been shown that the method allows an increase of the resistance of *Olea europea* against *Spilocaea oleagina* cast h. ugh and *Pseudomonas savastanoi*.

In an additional embodiment of the invention, the use of the compositions above disclosed as enhancers of the activity of macroelements, microelements, mesolements, nutritional catalyzers, fitoregulators and other active principles used in agriculture is disclosed.

In an additional embodiment of the invention, it is disclosed the use of the compositions of the invention for increasing the fertility and productivity to barren soils, sand soils or desert soils, as a consequence of monocultures, climate conditions.

In an additional embodiment, the use of the compositions of the invention for reducing the quantity of mineral fertilizers and of nitrogen and phosphate based fertilizers needed in agriculture is disclosed.

In a further embodiment, the use of the compositions of the invention for increasing the shelf-life of agricultural products is disclosed.

In an embodiment of the invention, the disclosed compositions are applied directly to the soil with fertigation (irrigation and fertilization).

In a different embodiment, the compositions are applied to one or more of leaves, roots and stem. For said purposes, the compositions are preferably liquid.

In certain embodiments, the formulations can also be in the form of a gel, emulsion, microemulsion, or microcapsule.

In an addition embodiment, the use of the compositions of the invention to increase the productivity of crops is disclosed. Productivity may be evaluated quantitatively considering the average weight of the plants or fruits.

In another embodiment, it is disclosed the use of the compositions of the invention to increase the resistance of crops to bacteria and fungi.

In another embodiment, the use of the compositions of the invention to reduce the use of known fertilizing compositions and especially of nitrogen and phosphate based fertilizers is disclosed.

In another embodiment, the use of the compositions of the invention to increase the efficacy of treatments of fertilizing compositions, pesticides, fungicides on crops is disclosed.

In another embodiment, the use of the compositions of the invention to increase and enhance germination of seeds is disclosed.

In another embodiment, the use of the compositions of the invention to increase the development of roots in plants is disclosed.

In another embodiment, the use of the compositions of the invention to increase the growth of plants comprising the step of using the compositions of any one of the preceding claims is disclosed.

In another embodiment, the use of the compositions of the invention by dipping or by spraying is disclosed.

In another embodiment, the use of the compositions of the invention at one or more of: before-transplantation, after-transplantation, after pruning, pre-ripening the fruits or during the whole growing cycle of the plant is disclosed.

In another embodiment, the use of the compositions of the invention to treat the plant seeds before sowing is disclosed.

In an additional embodiment, the compositions having the following % formula are disclosed:

| | |
|---|---|
| demineralized water | 66 |
| leonardite | 20 |
| citric acid | 3 |
| potassium bicarbonate | 10 |
| folic acid | 1 |
| Base humofolate | 22 |
| Pentahydrate sulphate copper | 8 |
| Ammonium hydrate 28 Be | 70 |
| demineralized water | 25 |
| Urea Technical (46% Ureic Nitrogen) having a very low content of biuret (<0.5-0.7%) | 44 |
| base humofolate | 31 |
| Monoammonium phosphate NP 12-52 (12% ammonia nitrogen; 52% phosphorus pentoxide) | 30 |
| Zinc sulphate (35% Zn) | 1 |
| Manganese sulfate (Mn 32%) | 1 |
| leonardite into fine powder | 36 |
| citric acid | 4 |
| Urea technique (46% N) | 7.5 |
| Potassium bicarbonate | 17 |
| Folic Acid | 0.5 |
| Boron Ethanolamine (11% B) | 3 |
| demineralized water | q.b. |
| Humofolate Base | 15 |
| Pentahydrate sulphate copper (Cu 25%) | 8 |
| Ammonium hydrate 28 Be | 32 |
| Phosphorus acid (salt 98-99%) | 25 |
| Demineralized water having ammonium nitrogen 5%, phosphorus pentaoxide $P_2O_5$ 16%, total Cu 2% | 20 |
| Humofolate Base | 25 |
| Neem oil | 30 |
| Karanja oil | 40 |
| emulsifier | 5 |
| Humofolate base | 20.9 |
| Ammonium polyphosphate NP 10-34 | 70 |
| Boron Ethanolamine 11% B | 9.1 |
| Humofolate Base | 27 |
| Boron Ethanolamine (11% B) | 73 |
| Humofolate Base | 40 |
| Kalium oxide (42% $K_2O$) | 60 |

Example 1

Humofolate Base in Liquid Form

The humofolate base, as above explained, is a fertilizer (a soil improver having specific activity) with a high content of humic acids.

The humofolate base can be used directly in the soil and/or for foliar application at an appropriate dosage or used in mixtures with mineral fertilizers containing simple or complex macro-, meso- and microelements, plant extracts, amino acids of different origin.

The composition of the humofolate base is, preferably, according to the following formula (% weight):

| % | component |
|---|---|
| 66 | demineralized water |
| 20 | leonardite finely minced with a title of organic carbon of biological origin, preferably >45% |
| 3 | citric acid |
| 10 | potassium bicarbonate |
| 1 | folic acid |

Production

In a sealed reactor equipped with a stirring system, preferably a double column one, and with adjustable speed and direction, half of the demineralized water, leonardite and citric acid are added while stirring.

The mixture is stirred for at least 2 hours at high speed, preferably varying the verse for better contact and homogenization of the citric acid and up to its complete solubilization.

After 1 hour of stirring at high speed, a solution with demineralized water (about 33%), potassium bicarbonate and folic acid, already prepared separately is added.

Said operation should be performed slowly in order to have a better extraction of the humic substances and avoiding the formation of foam.

The entire mass is stirred further for about 2-5 hours, preferably 4, at high speed and, preferably, reversing the direction of rotation so that the mass in the bottom of the extractor can also be treated. When stirring was concluded, the product was subjected to filtration with a special filter system or it is left to settle for about 3-7 days, preferably 5 days, so that insoluble particles could deposit.

Example 2

HUMOFOLATE Nitrogen Maximum—Liquid Formulation

The formulation of HUMOFOLATE Nitrogen Maximum is prepared using the following components:

| % | Component |
|---|---|
| 25 | demineralized water |
| 44 | Urea Technical (46% Ureic Nitrogen) having a very low content of biuret (<0.5-0.7%) |
| 31 | base humofolate |

In a reactor equipped with stirring, preferably propellers, water is added, preferably demineralized, and preferably at a temperature of 50° C. in order to allow a rapid dissolution of urea, which is added while stirring.

Once the urea is completely solubilized, liquid base humofolate is added while maintaining the mixture stirring and until the product is completely smooth and free of any smallest particles of urea.

Such a formulation can be marketed as a product (Humofolate Nitrogen Maximum liquid) having the following composition:

| % | Component |
|---|---|
| 20 | Ureic nitrogen |
| 3 | organic carbon of biological origin |

To said formulation there can also be added amino acids of vegetal or animal origin thus changing the title according to the technical and commercial needs.

Example 3

Humofolate BEST STARTER NPK 7-15-7 (Respective % or Fertilizing Units of Nitrogen (N), Phosphorus Pentoxide ($P_2O_5$), Potassium Oxide ($K_2O$) in the Formulation)+0.3% B+0.3% Mn+0.3% Zn Formulation in Granular or Micro Granular Product with Slow-Release.

The formulation is prepared, preferably as a microgranular formulation with granules from 0.5 to 1 mm in diameter, in order to allow a precise mechanized distribution at sowing.

The raw materials needed to make that product are as follows:

| % | component |
|---|---|
| 30 | Monoammonium phosphate NP 12-52 (12% ammonia nitrogen; 52% phosphorus pentoxide) |
| 1 | Zinc sulphate (35% Zn) |
| 1 | Manganese sulfate (Mn 32%) |
| 36 | leonardite into fine powder |
| 4 | citric acid |
| 7.5 | Urea technique (46% N) |
| 17 | Potassium bicarbonate |
| 0.5 | Folic Acid |
| 3 | Boron Ethanolamine (11% B) |
| q.b. | demineralized water |

Production Process:

In a blender, preferably 4-way blender, the following products are admixed:

leonardite, NP 12-54 monoammonium phosphate, zinc sulfate, manganese sulfate and urea.

The mass is well mixed and minced in a mill, preferably with pegs.

After grinding, the product is placed in a kneader, wherein citric acid and water, preferably demineralized water, have been added to form a muddy dough(slurry).

In the next step, the potassium bicarbonate and folic acid are diluted in demineralized water in order to create an alkaline medium enhancing the solubilization of folic acid, and added to the muddy mass.

Boron Ethanolamine is then added.

The entire mass was then homogenized to allow the total extraction of the humic substances from the leonardite and formation of stable complexes.

The mass is then dried, preferably in a rotary dryer, while maintaining proper moisture to permit granulation of the mass.

In a specific granulator or micro granulator the drying process is completed, preferably with an in fluid bed dryer, so as not to damage the grains.

To the mass binders, like for instance, carboxymethylcellulose or ligninsulfonate or other products can be added, according to the need and as found by the technician.

The final slow-release formulation has the following composition:

| % | component |
|---|---|
| 7 | total nitrogen (N), of which 3.6% ammoniacal nitrogen and 3.4% ureic nitrogen |
| 15 | phosphorus pentoxide ($P_2O_5$) |
| 7 | potassium oxide ($K_2O$) |
| 0.3 | boron (B) |
| 0.3 | zinc (Zn) |
| 0.3 | manganese (Mn) |

Example 4

Results

| crop | yield increase of the product % | Average reduction of fertilizer units administered % | Average reduction in agro-drug administered % |
|---|---|---|---|
| salad | 30 | 35 | 60 |
| lattuce | 14 | 55 | 70 |
| rocket | 12 | 55 | 70 |
| celery | 35 | 50 | 65 |
| valerian | 12 | 50 | 70 |
| tomato | 20 | 50 | 60 |
| Pepper | 18 | 50 | 50 |
| Eggplant | 16 | 40 | 50 |
| potato | 18 | 50 | 55 |
| Little bean | 25 | 50 | 60 |
| Bean | 15 | 50 | 60 |
| Cucumber | 22 | 60 | 70 |
| Radish | 15 | 55 | 70 |
| Squash | 25 | 55 | 70 |
| Carrot | 10 | 40 | 60 |
| Strawberry | 23 | 50 | 60 |
| Watermelon | 14 | 50 | 55 |
| Melon | 13 | 40 | 60 |
| Wheat | 12 | 40 | 40 |
| Barley | 11 | 40 | 50 |
| Quinoa | 26 | 50 | 65 |
| Corn | 20 | 40 | 50 |
| Soybeans | 16 | 50 | 60 |
| Rape | 18 | 40 | 50 |
| Sunflower | 16 | 50 | 50 |
| Sugar beet | 14 | 40 | 40 |
| Rice | 14 | 40 | 50 |
| Peanuts | 14 | 40 | 50 |
| Tobacco | 13 | 60 | 80 |
| Plum | 15 | 60 | 60 |
| Kiwi | 18 | 40 | 65 |
| Apple | 18 | 50 | 55 |
| Pear | 15 | 50 | 55 |
| Banana | 13 | 50 | 60 |
| Cherry | 10 | 40 | 65 |
| Peach | 12 | 40 | 50 |
| Apricot | 10 | 50 | 50 |
| Papaya | 13 | 50 | 60 |
| Mango | 12 | 40 | 60 |
| Pineapple | 14 | 40 | 50 |
| Pomegranate | 12 | 40 | 50 |
| Berries (blackberry, raspberry, blueberry) | 10 | 50 | 70 |
| Grapevine | 14 | 50 | 60 |
| Citrus | 12 | 40 | 60 |
| The | 20 | 40 | 60 |
| Coffee | 16 | 40 | 60 |
| Cocoa | 13 | 40 | 60 |

Example 5

Liquid Formulation of Humofolates on the Culture of Olive (*Olea europea*—Cultivar "Itrana")

BACSTONE HUMOFOLATES (invention humofolate liquid formulation)—composition:

| | |
|---|---|
| Base humofolate | 22% |
| Pentahydrate sulphate copper 25% Cu | 8% |
| Ammonium hydrate 28 Be | 70% |

The Bases humofolate comprises 2% Cu and 14% nitrogen (from ammonium hydrate).

Cupravit Blue WG 35—Bayer—composition

| |
|---|
| copper oxychloride formulation (Cu 35%) |

Interventions schedule in culture plan:

| | |
|---|---|
| I | immediately after pruning |
| II | on drupes a caliber similar to a grain of pepper |
| III | on drupes with a caliber of 50% compared to the size of the final collection |
| IV | pre-ripening of the fruit |

Interventions in culture plan with BACSTONE HUMOFOLATE—treatment A

| | |
|---|---|
| I | 7 kg/hectar (ha) of Bacstone, corresponding to 140 g/ha of total metal copper, in 1000 liters of water/ha have been distributed by means of a driven atomizer, for uniformly wetting the plant (leaves, branches and stem) |
| II | 6 kg/ha of Bacstone, corresponding to 120 g/ha of total metal copper, in 1000 liters of water/ha have been distributed by means of a driven atomizer capable of wetting uniformly the plant (leaves, branches and stem) |
| III | 6 kg/ha of Bacstone, corresponding to 120 g/ha of total metal copper, in 1000 liters of water/ha distributed by means of driven atomizer capable of wetting uniformly the plant (leaves, branches and stem) and preserving it from infections bacterial and fungal |
| IV | 6 kg/ha of Bacstone, equal to 120 g/ha of total metal copper, in 1000 liters of water/ha distributed by means of driven atomizer capable of wetting uniformly the plant (leaves, branches and stem) |

Interventions in culture plan with CUPRAVIT BLUE WG 35—treatment B:

| | |
|---|---|
| I | 4 kg/ha of Cupravit Blue 35 WG, microgranular fungicidal water dispersible, based on the form of Copper oxychloride 35% of Copper metal, equal to 1.40 kg/ha of total copper metal, in 1000 liters of water/ha for distributed means of atomizer driven able to wet uniformly throughout the plant (leaves, branches and stem) |
| II | 4 kg/ha of Cupravit Blue 35 WG, microgranular fungicidal water dispersible, based on the form of Copper oxychloride 35% of Copper metal, equal to 1.40 kg/ha of total copper metal, in 1000 liters of water/ha for distributed means of atomizer driven able to wet uniformly throughout the plant (leaves, branches and stem) |
| III | 4 kg/ha of Cupravit Blue 35 WG, microgranular fungicidal water dispersible, based on the form of Copper oxychloride 35% of Copper metal, equal to 1.40 kg/ha of total copper metal, in 1000 liters of water/ha for distributed means of atomizer driven able to wet uniformly throughout the plant (leaves, branches and stem) |
| IV | 4 kg/ha of Cupravit Blue 35 WG, microgranular fungicidal water dispersible, based on the form of Copper oxychloride 35% of metal Copper, equal to 1.40 kg/ha of total copper metal, in 1000 liters of water/ha for distributed means of atomizer driven able to wet uniformly throughout the plant (leaves, branches and stem) |

Results

During one year a total of only 500 g/ha copper metal was used with humofolate treatment instead of 5.6 kg/ha of copper metal using Cupravit, with a reduction by 91% of used copper metal, according to the following table:

TABLE 1

| quantity of copper used expressed as Kg/ha | | |
|---|---|---|
| I intervention | Treatment A | 0.14 |
| | Treatment B | 1.40 |
| II intervention | Treatment A | 0.12 |
| | Treatment B | 1.40 |
| III intervention | Treatment A | 0.12 |
| | Treatment B | 1.40 |
| IV intervention | Treatment A | 0.12 |
| | Treatment B | 1.40 |
| TOTAL | Treatment A | 0.50 |
| | Treatment B | 5.6 |
| | Reduction in copper | 91% |

At the same time, protection of the crop from fungal (*Spilocaea oleagina* cast h. ugh) and bacterial infections (*Pseudomonas savastanoi*—olive knot) and improvement in the quality of the fruit were achieved.

The plants treated with treatment A are healthy and with high vigor, significantly higher than those of the group treated with treatment B.

Example 6

Liquid Formulation of Liquid Humofolates on the Culture of Cicoria Catalonia (Celection "Gaeta")

Tested Formulations:

Invention Base Humofolate

Liquid Humus™ (Actagro, LLC.), Biola—California) as disclosed in the U.S. Pat. No. 4,698,090, which comprises 22% of organic acids from leonardite.

Intervention schedule in culture plan:

| | |
|---|---|
| 1. | dipping of plants |
| 2. | 7 days post - transplant |
| 3. | During the whole cycle, starting from the 35th day after transplantation |

Intervention schedule in culture plan with humofolates—treatment C:

| | |
|---|---|
| 1. | A water solution of Base Humofolate 500 g/100 L was prepared. |

| | |
|---|---|
| | Plants have been dipped in the solution by means of immersion. The above treatment was intended to encourage a strong development of roots. |
| 2. | A mixture has been prepared: |
| | 2 kg/500 m²     ammonium polyphosphates in liquid formulation NP 10-34 |
| | 1.5 kg/500 m²     Base humofolate |
| | The mixture was spread out with localized fertigation systems |
| | The same treatment was performed after 14 days. |
| 3. | The fertilization was administered via localized irrigation, with Base Humofolate at doses of |
| | 1.5 kg/500 m²     Urea 46% Nitrogen |
| | 1.5 kg/500 m²     Potassium Nitrate NK 13-46 |
| | 1.5 kg/500 m²     Base humofolate |
| | Four operations have been performed, the first three with intervals of 14 days from each other and the fourth after 10 days from the third treatment. |

Intervention schedule in culture plan with LIQUID HUMUS™ (ACTAGRO, LLC.)—treatment D:

| | |
|---|---|
| 1. | Preparation of a solution in water of Liquid Humus at doses 500 g/100 Liter of water; plants have been dipped in said solution by immersion. The above treatment was intended to encourage a strong root development, minimizing stress post-transplant. |
| 2. | A mixture has been prepared: |
| | 2 kg/500 m²     ammonium polyphosphates in liquid formulation NP 10-34 |
| | 1.5 kg/500 m²     Liquid Humus ™ (Actagro) |
| | The mixture was spread out by localized fertigation systems. |
| | The same treatment was performed after 14 days. |
| 3. | Fertilization was administered by means localized fertigation with Liquid Humus ™ at doses of: |
| | 1.5 kg/500 m²     Urea 46% Nitrogen |
| | 1.5 kg/500 m²     Potassium Nitrate NK 13-46 |
| | 1.5 kg/500 m²     Liquid Humus ™ (Actagro) |
| | There were performed four operations: the first three with intervals of 14 days from each other and the fourth after 10 days from the third treatment. |

The cultures treated with treatment D showed a delay of 8 days, which equals a difference in weight/plant of about 20% in favor of the plants treated with treatment C.

Analysis Physical-Chemical of Soil Before and After Testing

Before implantation ($t_0$) and after harvesting ($t_{end}$), soil samples were collected at a depth of 10-30 cm in the manner provided for in the Official Methods of Sampling (D.M 13/09/1999 of the Minister for Agriculture Politics: "APPROVAZIONE DEI METODI UFFICIALI DI ANALISI CHIMICA DEL SUOLO" published on the Official Italian Gazette, Ordinary Supplement N.248 of 21/10/1999).

From the physico-chemical analyzes, carried out following the analytical protocols proposed in the Official Methods the values shown in Table below were collected.

The water used for fertigation was provided by the Consortium of FONDI (LT) and Monte San Biagio (LT) and found not to alter the data.

TABLE

Chemical-physical analysis of soils

| | $t_0$ | $t_{end}$ | |
|---|---|---|---|
| | — | Treatment C | Treatment D |
| Skeleton | 5 | 5 | 5 |
| Sand (%) | 10 | 10 | 10 |
| Silt (%) | 12 | 12 | 12 |
| clay (%) | 73 | 73 | 73 |
| texture | clay | clay | clay |
| pH | 7.5 | 7.6 | 7.4 |
| Ec (mS) | 0.268 | 0.272 | 0.254 |
| Total limestone | 2.4 | 2.4 | 2.4 |
| S.O. (%) | 3.27 | 3.34 | 3.78 |
| tot N (%) | 0.25 | 0.26 | 0.26 |
| P (ppm) | 32 | 31 | 31 |
| Fe (ppm) | 18 | 16 | 15 |
| Mn (ppm) | 12 | 12 | 12 |
| Cu (ppm) | 3.8 | 3.9 | 3.5 |
| Zn (ppm) | 2.4 | 2.6 | 2.3 |
| Ca (ppm) | 4620 | 4540 | 4480 |
| Mg (ppm) | 418 | 389 | 402 |
| K (ppm) | 338 | 346 | 362 |
| Na (ppm) | 89 | 108 | 96 |

Results

Plants treated with treatment C came into production with eight days earlier than those treated with treatment D.

Thus, the use of the compounds of the invention allows anticipating harvest by 8 days.

Plants treated with treatment C did not suffer any stress during transplant, in contrast to those treated with Liquid Humus™ (Actagro), which suffered post-transplant stress.

The plants treated with treatment C showed during the vegetative cycle a difference of growth significantly higher than those treated with treatment D in terms of weight, size and photosynthetic activity; the latter demonstrated by a more marked green coloring than the plant as well as a relief Spad.

Moreover, a better compatibility of Humofolate compared to the compatibility of Liquid Humus (Actagro) with Urea 46% N and nitrate potassium NK 13-46 was shown.

In addition, an increase of production was shown:

| | Total quantity of plants | Plant average weight |
|---|---|---|
| Treatment C | 2,760 kg | 1,380 g/plant |
| Treatment D | 2,420 kg | 1,210 g/plant |
| increase in production | 14.04% | |

Example 7

Liquid Formulation of Liquid and Microgranules Humofolates on the Culture of Squash (Cultivar Greyzini F1, Company Seminis) in Greenhouse Tested Compositions:

Humofolate Base

Humofolate Best Starter NPK 7-15-7+0.3% B+0.3% Mn+0.3% Zn

HUMOFOLATE Humophos MAXIMUM NP

HUMOFOLATE SHIELD MAXIMUM

| Shield humofolate composition (weight %) | |
|---|---|
| Humofolate Base | 25% |
| Neem oil | 30% |
| Karanja oil | 40% |
| emulsifier | 5% |

| NPK HUMOFOLATE Best Starter NPK 7-15-7 + B + Mn + Zn starting composition | |
|---|---|
| Monoammonium phosphate NP 12-52 (12% ammonia nitrogen; 52% phosphorous pentoxide) | 30 |
| Zinc sulphate (35% Zn) | 1 |
| Manganese sulfate (Mn 32%) | 1 |
| leonardite into fine powder | 36 |
| citric acid | 4 |
| Urea technique (46% N) | 7.5 |
| Potassium bicarbonate | 17 |
| Folic Acid | 0.5 |
| Boron Ethanolamine (11% B) | 3 |
| demineralized water | q.b. |

| HUMOFOLATE Humophos MAXIMUM NP 7-23 + 1 B | |
|---|---|
| Humofolate base | 20.9% |
| Ammonium polyphosphate NP 10-34 | 70% |
| Boron Ethanolamine 11% B | 9.1% |

Interventions schedule in culture plan:

| 1. | Before transplantation |
|---|---|
| 2. | Post - transplant |
| 3. | During the whole cycle from the beginning of production for the entire production cycle |

Fertilization schedule with humofolate—treatment E:

1. 250 kg/ha of NPK Best Starter 7 - 15-7 + 0.3 B + 0.3 Mn + 0.3 Zn in a microgranular slow-release formulation with granules having a diameter of 0.5 to 1.2 mm
2. 50 kg/ha of HUMOFOLATE Humophos MAXIMUM NP 7-23 + 1% B in the liquid formulation distributed with localized fertigation system
3. 25 kg/ha of Humofolate Base in liquid formulation added with 30 kg/ha potassium nitrate NK 13-46 in soluble powder formulation has been distributed weekly with a localized fertigation
Treatment have been performed with resistance inducers based on Humofolate as below:
.5 kg/ha for foliar application HUMOFOLATE Booster Maximum distributed every 10 days during the entire crop cycle with zero deficiency of the harvest.
.5 kg/ha Shield Humofolate for foliar application produced with Humofolate Base and with extracts of *azadirachta indica* and *pongamia glabra*.
HUMOFOLATE Shield MAXIMUM is a specialty of Humofolate and plant extracts for the prevention of fungal infections by powdery mildew and combat infestations of insects such as aphids, whiteflies, thrips and mites.
In addition, the same formulation was used in localized fertigation at doses of 20 kg/ha also to prevent the infestation of nematodes on root system.
Two interventions performed with Shield Humofolate in a localized fertigation every 20 days one from the other.
Two other applications have been carried out in spring (during periods of high risk of attack by nematodes).

For foliar applications of Humofolate Shield MAXIMUM and Humofolate Booster MAXIMUM were used 1000 liters of water/ha.

Fertilization schedule—treatment F:
Based on the results of soil analysis (reported below in Table 1) was adopted the following fertilization plan.
Tested Compositions:

| Nitrophoska Gold | |
|---|---|
| TOTAL NITROGEN | 15% |
| of which: | |
| Nitric nitrogen | 2.5% |
| Ammonia nitrogen | 7.5% |
| Nitrogen isobutylidene diurea (ISODUR) | 5% |
| Phosphorus pentoxide ($P_2O_5$) | 9% |
| Potassium oxide ($K_2O$) | 15% |
| Magnesium oxide (mgo) | 2% |
| Sulfur trioxide | 20% |
| Iron | 0.3% |
| Boron | 0.01% |
| Copper | 0.002% |
| Manganese | 0.01% |
| Zinc | 0.002% |

| 1. | 1500 kg/ha of NPK Nitrophoska Gold 15 - 9 - 15 + 2 MgO + B + Cu + Fe + Mn + Zn in granular formulation of the company Compo distributed throughout the soil with manure spreaders orbital |
|---|---|
| 2. | 50 kg/ha of monoammonium phosphate NP 12-61 formulation in saline added with 30 kg/ha of Glucoumato Base 72 L1 (Fertirev Srl Italy) in liquid form with localized fertigation |
| 3. | 25 kg of Glucoumato Base 72 L1 (Fertirev Srl, Italy) added to 30 kg/ha of potassium nitrate NK 13-46 in soluble powder formulation distributed with localized fertigation. |

During the growth period of the plants were carried out interventions with agrochemicals indicated below:
3 kg/ha of Previcur systemic fungicide based on Propamocarb hydrochloride 66.5% with intervention up to 20 days before harvesting.
For nematodes it was administered 10 days post-transplant Vydate 10 L DuPont nematicide based on oxamyl at doses of 20 liters/ha.
To control powdery mildew, treatments were carried out with WG Folicur (Bayer) systemic fungicide, triazole at doses of 500 g/ha by spraying the plants with a cadence of 14 days throughout the crop cycle.
For the control of aphids and whiteflies was used Decis Jet (Bayer) at doses of 1 liter/ha with a cadence of 14 days.
For the application of crop protection products mentioned have been used 1000 liters of water/ha.

Physical and Chemical Analysis of Soil Before and After Testing

Before implantation ($t_0$) and after harvest ($t_{end}$) soil samples were collected at a depth of 10-30 cm in the manner provided for in the Official Methods of sampling.

The values shown in Table 1 were collected from the physico-chemical analyzes carried out following the analytical protocols proposed in the Official Methods.

The water used for fertigation was provided by the Consortium of the Remediation of Fondi (LT) and Monte San Biagio (LT) and found not to alter the results.

TABLE 1

Chemical-physical analysis of soils

|  | $t_0$ | $t_{end}$ | |
| --- | --- | --- | --- |
|  | - | Treatment F | Treatment E |
| Skeleton | Traces | Traces | Traces |
| Sand (%) | 17 | 17 | 17 |
| Silt (%) | 18 | 18 | 18 |
| Clay (%) | 65 | 65 | 65 |
| Texture | clay | clay | clay |
| pH | 7.4 | 7.6 | 7.2 |
| Ec (mS) | 0.343 | 0.418 | 0.289 |
| Total limestone (%) | 2.1 | 2.1 | 2.2 |
| S.O. (%) | 3.12 | 3.23 | 4.18 |
| N tot (%) | 0.22 | 0.21 | 0.21 |
| P (ppm) | 20 | 27 | 23 |
| Fe (ppm) | 15 | 15 | 17 |
| Mn (ppm) | 16 | 16 | 16.1 |
| Cu (ppm) | 3.5 | 3.8 | 3.9 |
| Zn (ppm) | 3.3 | 3.7 | 3.4 |
| Ca (ppm) | 4820 | 5102 | 5080 |
| Mg (ppm) | 476 | 524 | 518 |
| K (ppm) | 308 | 401 | 392 |
| Na (ppm) | 84 | 102 | 98 |

Results

The crop of squash cultivars Greyzini F1 (company Seminis) has been cultivated for a total of 181 days. The pepos were collected at commercial maturity with the flower fully open as required by the market for this cultivar.

Plants treated with treatment E came into production 3 days in advance and the fruits appeared more homogeneous with resistant flowers and with a better shelf-life.

The harvests were performed 3 times a week for a total of 72 harvests.

The plants treated with treatment E in liquid and micro granular showed a statistically significant increase in the number of fruit harvested per plant:

|  | Fruits per plants |
| --- | --- |
| Treatment E | 69 |
| Treatment F | 58 |
| increase | 18.96% |

In addition, at the end of culture, the plants treated with Treatment E were still in the production phase and capable of giving even more pepos valid from a commercial point of view.

Squash plants so treated are more balanced and with shorter internodes.

Moreover, the treatment allowed a drastic reduction in fertilizer units used in both pre-transplant fertilization and during the production cycle (post-transplant).

TABLE NO. 2

Units fertilizers used during the crop cycle

|  | N | $P_2O5$ | $K_2O$ | MgO |
| --- | --- | --- | --- | --- |
| Pre - transplant | | | | |
| Treatment E | 17.5 | 37.5 | 17.5 | 0 |
| Treatment F | 225 | 135 | 225 | 30 |
| Post - transplant | | | | |
| Treatment E | 3.5 | 11.5 | 0 | 0 |
| Treatment F | 6 | 30.5 | 0 | 0 |
| Productive phase | | | | |
| Treatment E | 78 | 0 | 276 | 0 |
| Treatment F | 78 | 0 | 276 | 0 |
| TOTAL | | | | |
| Total Treatment E | 99 | 49 | 293.5 | 0 |
| Total Treatment F | 309 | 165.5 | 501 | 30 |
| Reduction in fertilizing units | 67.96% | 70.39% | 41.41% | 100% |

As can be seen from the above table, there is a high reduction in the use of fertilizer thanks to treatment E; specifically:

|  | Reduction |
| --- | --- |
| N | 67.96% |
| P | 70.39% |
| K | 41.41% |

The cultivation of the plant group treated with Treatment E was carried out for the entire crop cycle without administration of agrochemicals, only resistance inducers and plant extracts characterized by a high share of repellency against insects and nematodes underground (HUMOFOLATE Shield MAXIMUM).

Thanks to the absence of the use of agrochemicals in the culture can detect the presence of pollinators insect.

It follows from the above it is clear that the technology of the invention is extremely environmental friendly highly sustainable and allows a significant increase in the quality and quantity of production of squash.

Example 8

Liquid and Microgranule Formulation of Humofolates on the Culture of Sugar Beet (*Beta vulgaris* Var *B. Saccharifera* 1.) Cultivars "DINARA" KWS Tested Sompositions:

HUMOFOLATE NPK Best Starter (see the above composition)

HUMOFOLATE Nitrogen MAXIMUM (see the above composition)

HUMOFOLATE Humophos MAXIMUM NP (see the above composition)

HUMOFOLATE Boron MAXIMUM:
  Humofolate Base 27%
  Boron Ethanolamine (11% B) 73%

HUMOFOLATE Kalium MAXIMUM:
  Humofolate Base 40%
  Kalium bicarbonate (42% $K_2O$) 60%

Fertilization humofolates schedule—treatment G:

| 1. At sowing | 35 kg/ha of NPK Best Starter 7 - 15-7 + 0.3 B + 0.3 Mn + 0.3 Zn in slow-release microgranular formulation of granules with a diameter of 0.5-1.2 mm distributed with pneumatic machine on the rows of sowing. |
| --- | --- |

-continued

| 2. During the growing season | 6 kg/ha of HUMFOLATE Nitrogen MAXIMUM in liquid formulation added with 3 Kg of HUMOFOLATE Boron MAXIMUM in liquid formulation distributed by means of spraying bar in mixture with the weeding and treatment against beet *cercospora* (*Cercospora beticola* sacc.) During the vegetative cycle are administered in total 12 kg/ha of HUMOFOLATE Nitrogen MAXIMUM and 6 kg/ha HUMOFOLATE Boron MAXIMUM. |
|---|---|
| 3. During cultivation | In addition, during the cultivation was performed in a nitrogen fertilization coverage applying 200 kg/ha of agricultural Granular Urea 46% N. |
| 4. 60 days and 30 days before harvest | In order to improve the production and the sugar degree two applications have been performed employing HUMOFOLATE Humophos MAXIMUM NP 7-23 + 1% B in the liquid formulation at a dose of 3 kg/ha and HUMOFOLATE Kalium MAXIMUM K 25 at a dose of 4 kg/ha in foliar application by spraying bar using a volume of water for application of 800 liters/ha. |

Fertilization schedule—treatment H

| 1. Before sowing | 350 kg/ha of diammonium phosphate NP 18 - 46 with fertilizer orbital distributed over the entire surface of the soil. |
|---|---|
| 2. During the growing season | The treatment of weeding and defense is made with the same formulations used in the experimentation with Humofolate with the addition of a formulation based on 5% of boron in the amount of 3 kg/ha (Borosol L9 Company Srl Fertirev, Italy). Treatment H does not comprise nitrogen foliar contributions and therefore there has been used 250 kg/ha of agricultural Urea equal to 115 units of total nitrogen. |

Physical and Chemical Analysis of Soil Before and After Testing

Before implantation of the test ($t_0$) and after harvest ($t_{end}$) soil samples were collected at a depth of 10-30 cm according to the procedures laid down in the Official Methods of sampling.

From the physico-chemical analyses carried out following the analytical protocols proposed in the Official Methods the values shown in Table 1 have been recovered.

The water used for fertigation comes from a feeding channel present in the factory and found not to alter the data.

TABLE 1

Chemical-physical analysis of soils

|  | $t_0$ | $t_{end}$ | |
|---|---|---|---|
|  | — | Treatment G | Treatment H |
| Skeleton | Traces | Traces | Traces |
| Sand (%) | 12 | 12 | 12 |
| Silt (%) | 54 | 54 | 54 |
| Clay (%) | 34 | 34 | 34 |
| Texture | slimy | slimy | slimy |
| pH | 7.6 | 7.5 | 7.7 |

TABLE 1-continued

Chemical-physical analysis of soils

|  | $t_0$ | $t_{end}$ | |
|---|---|---|---|
|  | — | Treatment G | Treatment H |
| Ec (mS) | 0.258 | 0.242 | 0.289 |
| Total limestone | 1.4 | 1.3 | 1.4 |
| S.O. (%) | 1.8 | 2.1 | 1.9 |
| N tot (%) | 0.14 | 0.14 | 0.15 |
| P (ppm) | 18 | 20 | 23 |
| Mn (ppm) | 30 | 29 | 28 |
| Zn (ppm) | 4.8 | 4.7 | 4.7 |
| K (ppm) | 246 | 225 | 238 |

Results

The cultivation of sugar beet (*Beta vulgaris* var *B. Saccharifera* L.) cultivars "DINARA" KWS was done for a total of 183 days.

|  | Crop | Sugar content |
|---|---|---|
| Treatment G | 680 q/ha | 17.2% |
| Treatment H | 545 q/ha | 16.4% |
| statistically significant increase | 24.77% | 0.8% |

The use of Humofolates allowed a drastic reduction in fertilizer units used in both fertilization background (pre-sowing) and in fertilizer during the growing season (post-sowing) as can be seen in Table n.2 below.

TABLE n. 2

Units fertilizers used during the crop cycle

|  | N | $P_2O_5$ | $K_2O$ | MgO |
|---|---|---|---|---|
| At sowing | | | | |
| Treatment G | 2.45 | 5.25 | 2.45 | 0 |
| Treatment H | 63 | 161 | 0 | 0 |
| During cultural cycle -foliar application | | | | |
| Treatment G | 2.16 | 0 | 0 | 0 |
| Treatment H | 0 | 0 | 0 | 0 |
| During cultural cycle -root application | | | | |
| Treatment G | 92 | 0 | 0 | 0 |
| Treatment H | 115 | 0 | 0 | 0 |
| 60 days and 30 days before harvesting | | | | |
| Treatment G | 0.42 | 1.4 | 1.6 | 0 |
| Treatment H | 0 | 0 | 0 | 0 |
| TOTAL | | | | |
| Total Treatment G | 97.03 | 6.65 | 4.05 | 0 |
| Total Treatment H | 178 | 161 | 0 | 0 |
| Reduction in fertilizing units | 45.48% | 95.87% | 0% | 0% |

From the values shown in Table N. 2 above it is shown that the technology of Humofolate is highly sustainable and has a low environmental impact since it enables to drastically reduce the use of phosphorus and nitrogen during the whole crop cycle and in particular:

| Reduction | |
|---|---|
| N | 45.48% |
| P | 95.87% |

Example 9

Technical Report on Liquid and Microgranule Formulation of Humofolates on the Culture of Wheat (Cultivar "ABATE")

Interventions schedule with humofolate—treatment I

| 1. | Sowing | it was layered the Best Starter NPK 7 - 15-7 + 0.3 B + 0.3 Mn + 0.3 Zn microgranular sustained release formulation with granules with a diameter of 0.5-1.2 mm in the product hopper having a specific weight similar to that of the seed wheat (81 kg - 83/hl) at doses of 40 kg/ha |
| 2. | During the crop cycle | In mixture with the foliar defense and weeding were performed three interventions with HUMOFOLATE Nitrogen MAXIMUM in liquid formulation at doses of 7 kg/ha per application for a total of 21 kg/ha. As nitrogen source urea 46% nitrogen was used in the amount of 200 kg/ha of nitrogen equal to 92 units divided into two doses: 50% in the extension phase and the remaining 50% in the boot phase. During the production cycle have been used fungicides for the control of rust and septoria. |

Intervention schedule—treatment L:

Based on the results of soil analysis (reported below in Table) the following fertilization plan was adopted.

| 1. | Pre-sowing | Over the entire surface diammonium phosphate fertilizer NP 18-46 in the dose of 300 kg/ha has been administered with the orbital. |
| 2. | Coverage | There was employed 250 kg/ha of Urea Agricola 46% nitrogen in granular formulation for a total of 115 units of nitrogen divided into two doses: 50% in the extension phase and the remaining 50% in the boot phase. During the crop cycle were used fungicides for the control of rust and septoria. |

Physical and Chemical Analysis of Land Before and After Testing:

Before implantation of the test ($t_0$) and after harvest ($t_{end}$) soil samples were collected at a depth of 10-30 cm in the manner provided for in the Official Methods of Sampling.

The physico-chemical analyzes carried out following the analytical protocols proposed in the Official Methods the results of Table 1 were collected.

TABLE 1

Chemical-physical analysis of soils

| | | $t_{end}$ | |
|---|---|---|---|
| | $t_0$ | Treatment I | Treatment L |
| Skeleton | Traces | Traces | Traces |
| Sand (%) | 11 | 11 | 11 |
| Silt (%) | 58 | 58 | 58 |
| Clay (%) | 31 | 31 | 31 |
| Texture | slimy | slimy | slimy |
| pH | 7.4 | 7.3 | 7.3 |
| Ec (mS) | 0.218 | 0.187 | 0.232 |
| Total limestone | 1.2 | 1.2 | 1.2 |
| S.O. (%) | 1.3 | 1.4 | 1.3 |
| N tot (%) | 0.27 | 0.25 | 0.29 |
| P (ppm) | 29 | 31 | 32 |
| Mn (ppm) | 22 | 23 | 22 |
| Zn (ppm) | 3.7 | 3.8 | 3.4 |
| K (ppm) | 223 | 197 | 208 |

Results

The cultivation of wheat cultivars "Abate" was carried for a total of 260 days.

| | Crop |
|---|---|
| Treatment I | 92 q/ha |
| Treatment L | 87 q/ha |
| increase | 5.74% |

The treatment with Treatment I has allowed a drastic reduction of the fertilizer units used during the production cycle as shown in the table below.

TABLE NO. 2

| Units fertilizers used during the crop cycle | | | | |
|---|---|---|---|---|
| | N | $P_2O_5$ | $K_2O$ | MgO |
| At sowing | | | | |
| Treatment I | 2.8 | 6 | 2.8 | 0 |
| Treatment L | 54 | 138 | 0 | 0 |
| During the cultivation cycle - foliar intervention | | | | |
| Treatment I | 3.8 | 0 | 0 | 0 |
| Treatment L | 0 | 0 | 0 | 0 |
| During the cultivation cycle - soil intervention | | | | |
| Treatment I | 92 | 0 | 0 | 0 |
| Treatment L | 115 | 0 | 0 | 0 |
| TOTAL | | | | |
| Total Treatment I | 98.6 | 6 | 2.8 | 0 |
| Total Treatment L | 169 | 138 | 0 | 0 |
| Reduction in fertilizer units | 41.65% | 95% | 0% | 0% |

The values of Table n.2 shows that the Humofolate technology is highly sustainable and has a low environmental impact since the application of the formulations Humofolate technology has allowed us to drastically reduce the use of phosphorus and of nitrogen during the whole crop cycle, in particular:

| Reduction | |
|---|---|
| P | 95% |
| N | 41.65% | while increasing the production of the crop of wheat cultivar Abate.

From the above description, the advantages of the present invention will be evident to those skilled in the art.

First of all, the formulations according to the invention have very high functionality, allowing improvement of the quality and the quantity of treated cultures compared to fertilizer compositions known in the art.

For example, plants treated according to the invention develop a strong root apparatus, thanks to an homogeneous absorbing of nutrients from the soil; they also show a more homogeneous growth and development of the leaves, flowers and of the stems between internodes.

In addition, there are greener leaves, numerous flowers and fruits and ripening times is achieved in a shorter period of time.

In addition, the vitamin and antioxidants content in fruits and vegetables proved to be increased. Also, the products have an improved and longer shelf-life.

From the point of view of quantity, the evaluation is performed considering the average weight of the plants or fruits.

The present invention also makes it possible to obtain compositions having high effectiveness and environmentally sustainable, thanks to the use of active principles, which are not toxic to humans, animals and the ecosystem.

In addition, for the preparation of the fertilizing compositions above disclosed extracting compounds which do not damage the fossil raw materials are used, like citric acid; in fact, the functional groups present in the organic fractions are not altered and can therefore fully act both in foliar and in soil application.

In particular, the citric acid is capable of forming complexes having high biological activity, especially when the humofolate base formulation is used for preparing specific compositions.

The use of folic acid also increase the availability of nutrients as it increases their absorbing. The formulations obtained with the present invention may be used in any soil and climate conditions both alone and in the mixture with macroelements, microelements, meso-elements, nutritional catalysts, plant growth regulators (auxins, cytokinins, gibberellins), thereby greatly improving their effectiveness and persistence.

Moreover, the invention formulations allow enrichment of soils depleted by monoculture techniques, barren lands, sterile soils, sandy soils and desert. The disclosed formulations shown to allow a reduction in the use of fertilizers, mineral or synthetic fertilizers and particularly the use of nitrates and phosphates on crop unit up to 70%, while at the same time increasing the production of fruit crops, industrial crops and bioenergetic crops (like soybean, rapeseed, sunflower, Jatropha curcas etc.). In addition, the water absorbing fertilizing compositions above disclosed allow a reduction in water irrigation, which can account to 20%, as they inhibit the evaporation of water and nutritional substances in the soil.

Furthermore, the above specific formulations can be used as resistance inducers for enhancing the endogenous resistance of plants toward fungi and bacteria.

The formulations of the invention are characterized by a pH between 6-7.5, that renders them completely compatible in any pedological condition without showing phytotoxicity (typical condition of known humates having a pH from 9 to 11); in addition, said pH allows the compositions of the invention to be admixed with other compounds for agricultural use exhibiting vehicle properties.

When used for foliar application, even admixed with other fertilizers, they increase the permeability of stomas and apertures on the leaf surfaces.

On the other hand, when used for root application, they show an auxine-like activity on the adventitious roots.

The products of the invention can also be formulated as liquid, gel, emulsions, microemulsions, or solid formulations, granulates, microgranulates, microencapsulated, according to the need.

In addition, solid formulations like granules and microgranules can be produced as slow-release formulations.

The invention claimed is:

1. A process for the preparation of a fertilizing composition comprising the steps of:
    a) preparing a muddy mixture of a fossil base material and water wherein the fossil base material and water are admixed in a ratio of between about 1 fossil base material to about 0.1 water and about 1 fossil base material to about 10 water, said fossil base material having at least 45% organic content and said fossil base material being selected from the group consisting of leonardite, lignite, peat humus, xylite, coal peat, brown coal and mixtures thereof;
    b) adding to said muddy mixture citric acid in an amount of between 1-7% (w/w) and stirring the obtained mixture until homogenization;
    c) adding to the mixture obtained from step b an alkaline solution of potassium bicarbonate in an amount of between 5-20% (w/w total mixture) and folic acid in an amount of between about 0.5 to about 6% (w/w).

2. The process according to claim 1, wherein in step a) the fossil base material is characterized by a granulometric size of between 100 and 200 mesh.

3. The process according to claim 1, wherein in step b) the citric acid is added as monohydrate citric acid.

4. The process according to claim 1, wherein the final composition has a pH of about 6.0-7.5.

5. The process according to claim 1, wherein in step a) there are added one or more substances capable of releasing macroelements, microelements, mesoelements, nutritional catalyzers, proteic hydrolyzed of animal or vegetal origin, one or more substances selected from the group consisting of insects repellents, fungicidal, fungistatic and nematodes, bactericidal and bacteriostatic compounds, plant growth regulators, complex fertilizers, water absorbing substances, and vegetable cakes obtained from the extraction of oils.

6. The process according to claim 1, wherein said water absorbing substances of natural origin or synthetic origin are added in a quantity comprised of between about 5-20% weight.

7. The process according to claim 1, further comprising a step d1) of subjecting the muddy composition obtained from step c) to granulation or pelletisation and further comprising a step e1) of drying.

8. The process according to claim 1, comprising after step c) a step d2) for separating solid particles and insoluble materials performed by filtration or decanting.

9. A fertilizing composition obtained with the process of claim 1.

10. The fertilizing composition of the claim 9, which is in the solid, liquid, gel emulsion, microemulsion or microencapsulated form.

11. The fertilizing composition according to claim 9, having a granule size of between 0.5-2.5 mm.

12. The fertilizing composition according to claim 9, which is a slow-release composition.

* * * * *